United States Patent [19]

Egler

[11] 4,091,922
[45] May 30, 1978

[54] CATHETER PACKAGE

[75] Inventor: Vernon C. Egler, Palatine, Ill.

[73] Assignee: The Kendall Company, Boston, Mass.

[21] Appl. No.: 734,859

[22] Filed: Oct. 22, 1976

Related U.S. Application Data

[63] Continuation-in-part of Ser. No. 578,227, May 16, 1975, abandoned.

[51] Int. Cl.² .................................................. B65D 83/04
[52] U.S. Cl. ........................................ 206/364; 206/332; 206/306; 206/382; 206/439; 206/443; 128/335.5; 206/591
[58] Field of Search ............... 206/364, 443, 439, 369, 206/330, 331, 332, 306, 380, 381, 382, 379, 363, 365, 591; 128/335.5

[56] References Cited

U.S. PATENT DOCUMENTS

| | | | |
|---|---|---|---|
| 1,280,264 | 10/1918 | Mapes | 206/381 |
| 1,350,294 | 8/1920 | Brown et al. | 206/381 X |
| 2,751,074 | 6/1956 | Ringlen et al. | 206/363 |
| 2,897,962 | 8/1959 | Zackheim | 206/369 |
| 3,010,540 | 11/1961 | Dahlen | 206/589 |
| 3,035,691 | 5/1962 | Rasmussen et al. | 206/364 |
| 3,227,265 | 1/1966 | Schneider | 206/382 |
| 3,468,471 | 9/1967 | Linder | 206/439 X |
| 3,472,369 | 10/1969 | Schuster | 206/439 |
| 3,642,123 | 2/1972 | Knox | 206/365 |
| 3,754,700 | 8/1973 | Bonk | 206/439 |

FOREIGN PATENT DOCUMENTS 1,022,088   3/1966   United Kingdom .................. 206/364

Primary Examiner—William Price
Assistant Examiner—Joseph M. Moy
Attorney, Agent, or Firm—Powell L. Sprunger

[57] ABSTRACT

A package for an elongated catheter comprising, an elongated container of a flexible material resistant to passage of bacteria. The container has at least one elongated generally linear cell extending longitudinally in the container, with the cell having a sufficient length to receive the catheter intermediate ends of the container. The cell also has cross-sectional dimensions of a size sufficiently large to receive the catheter and sufficiently small to maintain the catheter generally aligned in the cell. The container has a sufficient width to prevent excessive flexation of the container throughout a substantial longitudinal extent thereof. The container also has opening means communicating between the cell and the outside of the container. The package has means for closing the opening means, with the closing means being resistant to the passage of bacteria and permeable to the passage of a sterilization medium for sterilization of the catheter through the closing means.

29 Claims, 8 Drawing Figures

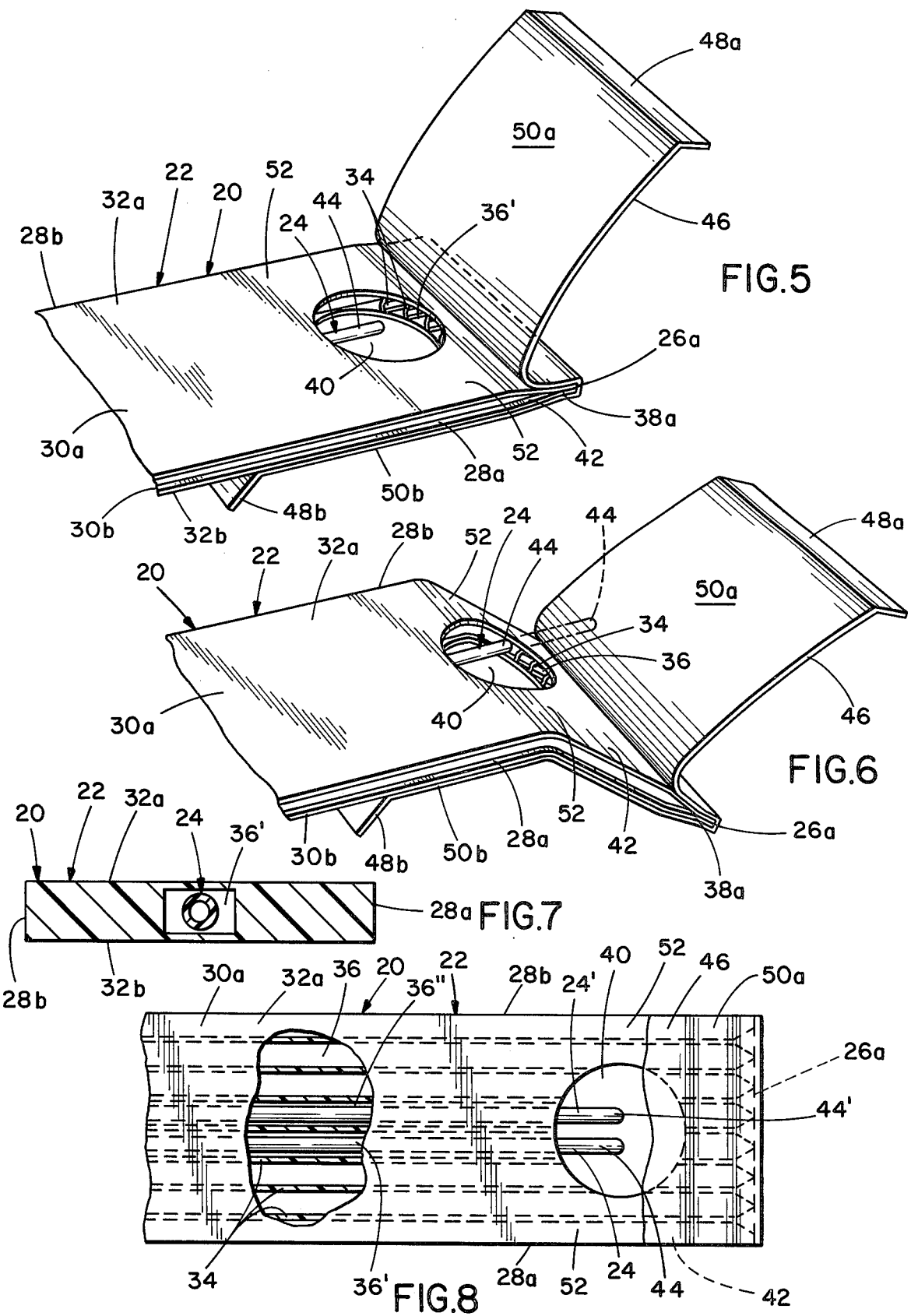

4,091,922

CATHETER PACKAGE

BACKGROUND OF THE INVENTION

This is a continuation-in-part of application Ser. No. 578,227, filed May 16, 1975, now abandoned.

The present invention relates to packages, and more particularly to packages for catheters.

Before the present invention, a various assortment of packages have been proposed for retaining catheters. After placement of one or more catheters in such packages, the interior of the package is sterilized, such as by ethylene oxide, and the sterile package is distributed to the user, for example at a hospital, where it is stored until use. Accordingly, the package must be readily susceptible to sterilization, and must maintain its contents in a sterile condition, possibly for an extensive length of time during storage, until the contents are used. The package should be inexpensive to reduce the over-all cost of package and contents to the user, and should be readily openable at the time of use.

Within the above constraints, satisfactory packages for certain catheters made from thermoplastic materials, such as ureteral catheters, have been particularly difficult to construct. Such catheters may form a permanent kink if bent sharply, or a permanent curved set if permitted to rest in a curved state in the package for an extended length of time. It is apparent that such kinked or curved catheters would normally be unsuitable for placement or use in a patient, and thus are worthless. Accordingly, the package should also maintain such catheters in a relatively linear condition to prevent formation of a permanent curved set in the catheters, and should be sufficiently rigid to prevent sharp bending and kinkage of the catheters. The solution to this packaging problem is further compounded by the considerable lengths of such catheters.

SUMMARY OF THE INVENTION

A principal feature of the present invention is the provision of a package of simplified construction and reduced cost for retaining a catheter.

The package of the present invention comprises, an elongated container of a flexible material resistant to passage of bacteria. The container has a pair of end edges, and a pair of side edges connecting the end edges. The container has at least one elongated generally linear cell extending longitudinally in the container, and, in a preferred embodiment, has a plurality of contiguous cells disposed laterally across the container. The one cell has a sufficient length to receive the catheter intermediate its ends, and has cross-sectional dimensions of a size sufficiently large to receive the catheter and sufficiently small to maintain the catheter generally aligned in the cell. The container has a sufficient width to prevent excessive flexation of the container throughout a substantial longitudinal extent thereof. The container also has opening means extending through the container and communicating between the one cell and the outside of the container, with the opening means being located adjacent one end of the container and spaced from the associated one end edge of the container, and with the opening means being located with one end of the catheter exposed in the opening means. The package has a sheet of material closing the opening means adjacent opposed outer surfaces of the container, with the sheet being resistant to passage of bacteria and permeable to the passage of a sterilization medium.

A feature of the present invention is that in the preferred embodiment the container is extruded from a thermoplastic material, and the ends of the cells may be closed by heat sealing the ends of the container.

Another feature of the invention is that the catheter may be readily placed in the one cell of the container for retention therein.

Yet another feature of the invention is that the sheet may be releasably secured to the container, such as by heat sealing the sheet to the outer surface of the container around the periphery of the opening.

Thus, a feature of the present invention is that the package of the present invention is readily formed in an inexpensive manner.

Another feature of the invention is that the inside of the package and the catheter may be readily sterilized through the sheet and the opening means.

Yet another feature of the invention is that the cell maintains the catheter in a relatively linear condition, and prevents the formation of a permanent curved set in the catheter prior to use.

Still another feature of the invention is that the container, although made of a flexible material, is sufficiently rigid to prevent excessive flexation of the container and formation of kinks in the catheter.

A feature of the present invention is that the sheet may be readily removed from a surface of the container to expose the one catheter end preparatory to use of the catheter.

Another feature of the invention is that an end portion of the container may be flexed about a region of weakness defined by the opening means in the container, in order that the one catheter end may be grasped for removal of the catheter from the package.

Further features will become more fully apparent in the following description of the embodiments of this invention and from the appended claims.

DESCRIPTION OF THE DRAWINGS

In the drawings:

FIG. 5 is a fragmentary perspective view of a sheet in the package being removed to expose an end of the catheter preparatory to use of the catheter;

FIG. 6 is a fragmentary perspective view illustrating an end portion of a container in the package being flexed to permit removal of the catheter from a cell in the container;

FIG. 7 is a sectional view of another embodiment of a catheter package of the present invention; and FIG. 8 is a fragmentary plan view, partly broken away, showing the catheter package of the present invention, with a plurality of catheters located in the package.

DESCRIPTION

Figure 1:
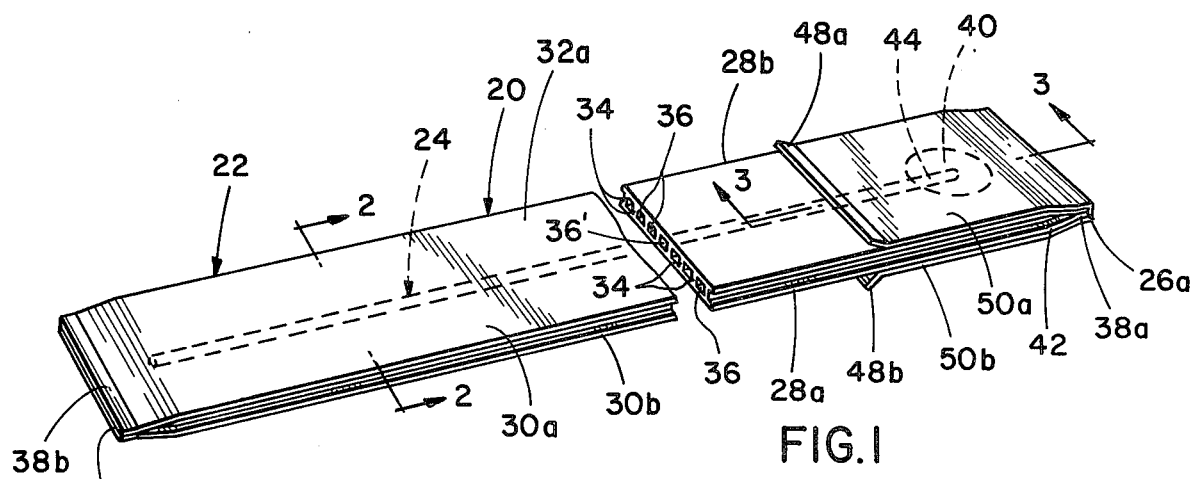
FIG. 1 is a fragmentary perspective view of a catheter package of the present invention.
Figure 2:
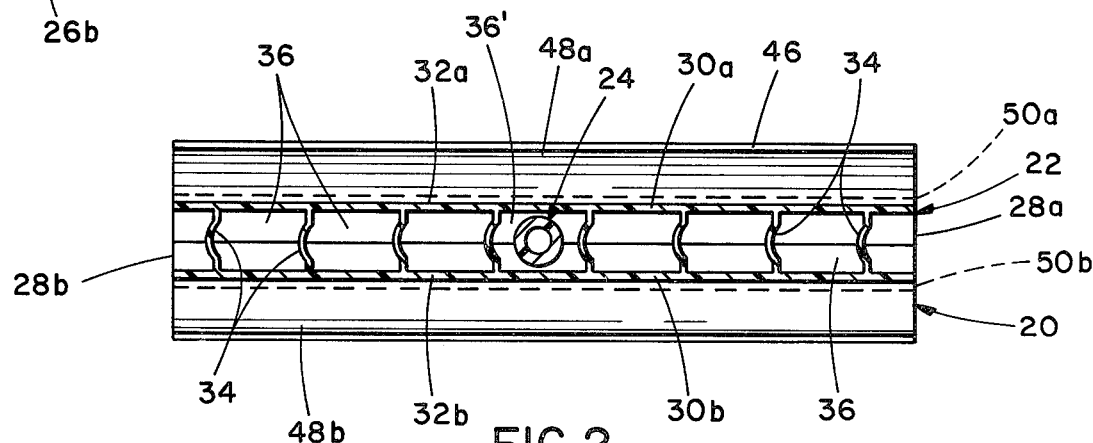
FIG. 2 is a sectional view taken substantially as indicated along the line 2—2 of FIG. 1.
Figure 3:
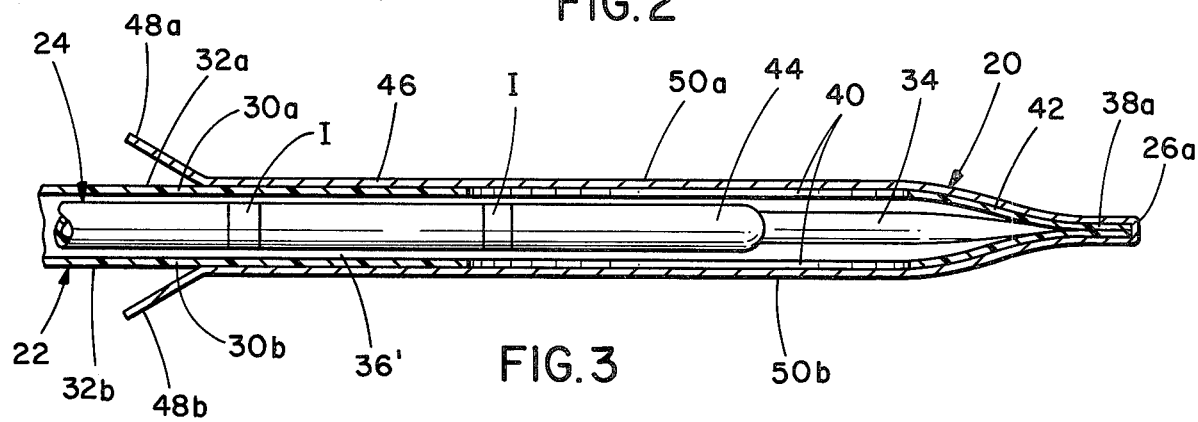
FIG. 3 is a fragmentary sectional view taken substantially as indicated along the line 3—3 of FIG. 1.

Referring now to FIGS. 1-3, there is shown a package generally designated 20 having an elongated container of flexible material designated generally 22 and a catheter generally designated 24 retained in the elongated container 22. The catheter 24, e.g., a ureteral catheter, may be of the type made from a thermoplastic material, such as polyurethane, polyvinylchloride, or polyethylene. As known, due to the nature of such materials the catheter is susceptible to kinkage if bent sharply, or to formation of a permanent curved set if permitted to rest for extended periods of time in a curved condition. The container 22 may be made of a thermoplastic material, such as polypropylene, and should be compatible with the materials of the catheter 24 to prevent migration of plasticizers between the container and catheter, as well as spaced inked markings I which may be placed on such catheters. A suitable selection of compatible materials for the package would be a polypropylene container 22 with a polyethylene catheter 24.

The elongated container 22 is extruded from the thermoplastic material and cut into lengths. As shown, the elongated container 22 has a pair of end edges 26a and 26b defining ends of the container, and a pair of side edges 28a and 28b connecting the end edges 26a and b and defining sides of the container. The container 22 has a pair of spaced webs 30a and 30b extending between the end edges 26a and b and the side edges 28a and b, with the webs 30a and b defining opposed outer surfaces 32a and 32b of the container 22. The container 22 also has a plurality of aligned and spaced ribs 34 connecting the webs 30a and b, with the ribs 34 extending longitudinally in the container between the end edges 26a and b. As best shown in FIG. 2, the webs 30a and b and ribs 34 define a plurality of elongated linear cells 36 extending substantially the length of the container 22, and as illustrated in FIGS. 1 and 3, the ends of the container 22 are closed adjacent the end edges 26a and b, such as by heat seals 38a and 38b, to close the ends of the cells 36 after placement of the catheter in the container.

As shown in FIGS. 1-3, the catheter 24 is retained in a cell 36' which is preferably located adjacent the lateral central region of the container 22. The cell 36' has cross-sectional dimensions slightly larger than the catheter in order that the catheter may be readily placed in the cell when the package is made. In a preferred embodiment of the package, the cross-sectional dimensions of the various cells in the container are approximately the same, such that the catheter may be placed in any suitable cell, as desired. Due to relatively close spacing between the walls of the cell and the catheter, the catheter is maintained in the cell 36' with the catheter being generally aligned with the walls of the cell or the cell itself.

Although the container 22 may be made of a flexible material, it will be apparent that the webs 30a and b and ribs 34 provide a structural rigidity for the container, and by a suitable selection of the container's width and the corresponding number of ribs in the container, excessive flexation of the container will be prevented. Thus, the container resists formation of a sharp bend in the webs 30a and b and ribs 34. If the ends of the container are flexed slightly and released, the container returns to its planar configuration with the cells in their linear configuration. In the package shown, the container has been selected to contain eight ribs, and has been found suitable to maintain the corresponding seven cells defined by the ribs in their linear condition.

Since the container prevents formation of sharp bends in the cell walls, it also prevents formation of kinks in the catheter. Additionally, since the catheter is aligned in the cell 36' and the container maintains the cell in a linear condition, the container also retains the catheter in a linear configuration. Thus, the container also prevents formation of permanent curved sets in the catheter, which otherwise might occur if the catheter is permitted to rest in a curved state for extended periods of time.

As shown in FIGS. 1, 3, and 8, the container 22 has an opening or opening means 40 extending through the container 22. The opening 40 communicates between the outside of the container and a plurality of the contiguous cells 36, including the cell 36' in which the catheter 24 is retained. The periphery of the opening 40 is spaced from the side edges 28a and b and the end edge 26a of the container 22, such that the opening 40 defines an end portion or section 42 of the container 22 intermediate the opening 40 and the end edge 26a for a purpose which will be described below. When placed in the cell 36', the catheter abuts against a tapered wall portion of the cell defined by the seal 38b adjacent the end edge 36b, and the distance of the container between the location of abutment and the opening 40 is selected such that one end 44 of the catheter is exposed in the opening 40.

As shown in FIGS. 1-3, a sheet 46 of material which is resistant to passage of bacteria is releasably secured to the opposed surfaces 32a and b of the container 22 to cover the opening 40 at both opposed surfaces of the container. The sheet 46 may extend between side edges 28a and b of the container, and the sheet may be conveniently heat sealed to the container around the peripheries of the opening. In a preferred embodiment, the sheet extends along the outer surface of the container between both ends of the opening and around the end edge 26a. The sheet 46 may have end portions which remain free of attachment to the container 22 in order to define a pair of grasping tabs 48a and 48b in the sheet.

The sheet 46 may be readily secured to the container 22 by placing the sheet against the container with its longitudinal midpoint located approximately at the end edge 26a of the container, with a first segment 50a of the sheet overlying the first surface 32a of the container 22, and with a second segment 50b of the sheet overlying the second surface 32b of the container. The container 22 and overlying sheet 46 may then be inserted into a heated die to heat seal the sheet segment 50a to the container surface 32a around the opening 40, and the sheet segment 50b to the container surface 32b around the opening 40.

After the sheet 46 has been secured to the container 22, the inside of the package, including the catheter 24, may be sterilized by passing a suitable sterilization medium through the sheet 46 and opening 40 at both opposed surfaces of the member 22. In a preferred embodiment, the sheet 46 may be made of a gas permeable material, such as Tyvek, a trademark of E. I. DuPont de Nemeurs, such that ethylene oxide may be passed through the sheet 46 to sterilize the catheter and inside of the package. Alternatively, the sheet may be made of a suitable material, such as paper, in order that the inside of the package may be autoclaved. As noted above, the sheet 46 is made of a material which is resistant to passage of bacteria, and the sterile package may be stored for extended lengths of times without contamination to the inside of the package and the catheter 24.

When it is desired to utilize the catheter, the user may grasp either of the tabs 48a or 48b to peel the corresponding sheet segments 50a or b from the associated outer surface of the container 22. As shown in FIG. 5, the user has removed the sheet segment 50a from the container surface 32a through use of tab 48a in order to expose the one end 44 of the catheter 24 in the opening 40. Alternatively, the user could remove the sheet segment 50b through use of tab 48a to expose the catheter end 44 in the opening 40 at the opposed surface 32b of the container 22.

As illustrated in FIG. 6, the user may then flex the end section 42 of the container 22 along a line or region of weakness 52 intermediate the opening 40 and the side edges 28a and b of the container. As will be apparent, the line of weakness 52 is defined by the opening due to the reduced amount of material in the container in this region. After the end section 42 has been bent along line 52, the one end 44 of the catheter 24 may be grasped by the user's sterile fingers, and the catheter may be removed from the cell in which it has been retained by pulling it forwardly from the cell. Accordingly, the package of the present invention also permits easy access to and removal of the catheter from the package, after which it may be used.

Figure 4:
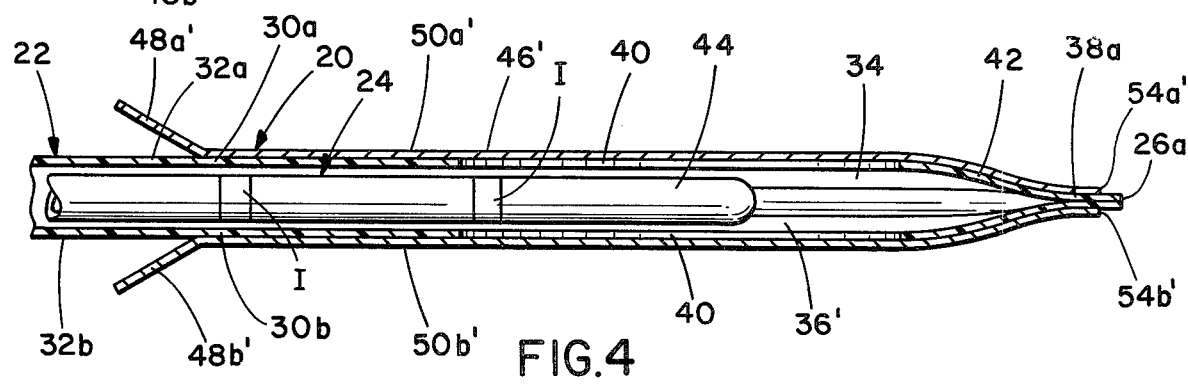
FIG. 4 is a fragmentary sectional view of another embodiment of the catheter package of the present invention.

Another embodiment of the present invention is illustrated in FIG. 4, in which like reference numerals designate like parts. In this embodiment, the segments 50a' and 50b' of the sheet 46' are separated from each other, such that end edges 54a' and 54b' of the sheet are located intermediate the opening 40 and the end edge 26a of the container 22. As before, the segments 50a' and b' may extend between the side edges of the package, and each of the segments 50a' and b' may have a grasping tab 48a' and 48b', respectively. As shown, the segment 50a' covers the opening 40 adjacent the surface 32a of the container 22, while the segment 50b' covers the opening 40 adjacent the surface 32b of the container. As previously described, either of the grasping tabs 48a' or 48b' may be grasped by the user to remove the corresponding segment 50a' or 50b' and expose the catheter end 44 at the associated surface 32a or 32b of the container 22.

Another embodiment of the present invention is illustrated in FIG. 7, in which like reference numerals designate like parts. In this embodiment, the container 22 has opposed laterally extending surfaces 32a and 32b, and a longitudinally extending cell 36' to receive the catheter 24, as before. However, in this embodiment the container 22 has only a single cell for retention of the catheter, while the remainder of the container intermediate the cell 36' and the side edges 28a and b of the container is of solid construction. As previously described, the walls of the cell 36' are closely spaced from the catheter 24 to maintain the catheter at a generally linear configuration, and prevent formation of a curved set in the catheter. The solid side portions of the container provide the container with sufficient rigidity to prevent excessive flexation of the container and formation of kinks in the catheter.

Another embodiment of the present invention is illustrated in FIG. 8, in which like reference numerals designate like parts. In this embodiment, the structure of the container 22 is substantially the same as that discussed in connection with FIGS. 1-3. The container has at least two cells 36' and 36" which communicate with the opening 40, and the cells 36' and 36" are preferably located in a lateral central region of the container 22. As shown, the package 20 has a pair of catheters received in the cells 36' and 36", with the catheter 24 being located in the cell 36', with the catheter 24' being positioned in the cell 36", and with the corresponding catheter ends 44 and 44' being exposed in the opening 40.

Both catheters may be removed from the package by removing a sheet segment and bending the container end section 42, as previously described. It will be apparent that any suitable number of catheters may be retained in the package, as desired, according to the requirements of a particular medical procedure during which the catheters are used.

The foregoing detailed description is given for clearness of understanding only, and no unnecessary limitations should be understood therefrom, as modifications will be obvious to those skilled in the art.

I claim:

1. A package comprising:
   an elongated catheter;
   an elongated extruded container of a flexible material resistant to passage of bacteria, said container having first and second ends, a pair of opposed sidewalls at least partially defining an elongated generally linear cell extending longitudinally in said container, said cell being slightly larger in cross-section and longer than said catheter and containing the catheter to maintain the catheter generally aligned in the cell, said container having a sufficient width to prevent excessive flexation of the container throughout a substantial longitudinal extent thereof, a pair of opposed outer walls defining a part of said cell, with both of said outer walls connecting and being of one-piece integral extruded construction with both of said sidewalls, and an opening extending through both the outer walls and cell communicating between said cell and the outside of the container, and with said opening itself defining a region of sufficient weakness in said container to permit flexation of an end portion of the container about the weakened region and permit grasping of said one catheter end for removal of the catheter from the package for use; and means for closing said opening, said closing means being resistant to the passage of bacteria and permeable to the passage of a sterilization medium for sterilization of the catheter through the closing means.

2. The package of claim 1 wherein the material of said container is compatible with the material of said catheter.

3. The package of claim 1 wherein said container is made from a thermoplastic material.

4. The package of claim 3 wherein said container is made from polypropylene.

5. The package of claim 1 wherein the ends of said container are closed to close the ends of said cell.

6. The package of claim 3 wherein the ends of said container are closed to close the ends of said cell, and the ends of said container are heat sealed to close the ends of said cell.

7. The package of claim 1 wherein said opening is located adjacent one end of the container.

8. The package of claim 7 wherein said opening is spaced from said one container end.

9. The package of claim 1 wherein said container has a pair of side edges connecting said first and second ends, and said opening is spaced from said side edges.

10. The package of claim 7 in which one end of the catheter abuts against a portion of the container adjacent the other end of the container when the catheter is placed in said cell, and in which the distance between the abutment portion of the container and a portion of the opening is approximately equal to the length of the catheter, whereby the other end of the catheter is located in the region of the opening when the catheter is placed in said cell.

11. The package of claim 10 wherein said opening is spaced from said one container end, said container has a pair of side edges connecting said first and second ends, said opening is spaced from said side edges, and in which said opening defines a lateral region of weakness in said container intermediate the opening and said side edges, whereby a section of said container intermediate said opening and said one container end may be bent about said weakness region to permit grasping of the other catheter end for removal of the catheter from the package and use.

12. The package of claim 1 in which said closing means comprises sheet means which closes said opening adjacent opposed laterally extending surfaces of said container.

13. The package of claim 12 wherein said sheet means comprises a sheet which extends between ends of said opening along the outer surface of the container and around said one container end.

14. The package of claim 13 wherein said sheet means comprises a sheet which is releasably secured to at least one surface of said container around the periphery of said opening.

15. The package of claim 12 wherein said sheet means comprises a pair of sheet segments, with each segment closing an end of said opening adjacent opposed outer surfaces of said container.

16. The package of claim 1 wherein said closing means comprises a sheet releasably secured to an outer surface of the container around the periphery of said opening.

17. The package of claim 16 wherein said sheet is heat sealed to the outer surface of said container.

18. The package of claim 16 wherein said sheet includes a tab which is free of attachment to said container to facilitate removal of said sheet from said container.

19. The package of claim 1 wherein said closing means comprises a sheet which is permeable to a sterilization gas.

20. The package of claim 1 wherein said container has a plurality of aligned cells disposed in a contiguous relationship laterally across said container.

21. The package of claim 20 wherein a multiplicity of said cells communicate with said opening.

22. The package of claim 21 wherein at least a second of said multiple cells has cross-sectional dimensions of a size to receive a second catheter.

23. The package of claim 20 wherein said plural cells have approximately equal cross-sectional dimensions.

24. The package of claim 1 wherein said container has a pair of side edges connecting said first and second ends, and a solid cross-section intermediate said cell and said side edges.

25. A package comprising:
an elongated catheter;
an elongated extruded container of a material resistant to the passage of bacteria, said container having a pair of opposed sidewalls at least partially defining a longitudinally extending cell of sufficient length to receive the catheter intermediate ends of the container, said cell being slightly larger in cross-section than the catheter and containing the catheter to retain the catheter generally aligned in the cell, said container being sufficiently rigid throughout a substantial length of the container to prevent excessive flexation of the container and catheter, said container having an opening adjacent one of its ends communicating between the outside of the container and said cell, and a pair of opposed outer walls defining a part of said cell, with both of said outer walls connecting and being of one-piece integral extruded construction with both of said sidewalls, and said opening extending through both the outer walls and cell, and with said opening itself defining a region of sufficient weakness in said container to permit flexation of an end portion of the container about the weakened region and permit grasping of said one catheter end for removal of the catheter from the package for use; and a sheet of material closing said opening, said sheet being resistant to the passage of bacteria and permeable to the passage of a sterilization medium for sterilization of the catheter through said sheet.

26. A package, comprising:
an elongated catheter;
an elongated extruded container of a material resistant to the passage of bacteria, said container having a longitudinally extending cell of sufficient length to receive the catheter intermediate ends of said container, said cell being slightly larger in cross-section than the catheter and containing the catheter, said container being sufficiently rigid throughout a substantial length of the container to prevent excessive flexation of the container and catheter, and said container comprising a pair of opposed outer walls defining a part of said cell and an opening extending through both the outer walls and cell and positioned adjacent to and spaced from one end of the container, with said opening communicating between the outside of the container and said cell at a location adjacent one end of the catheter, and with said opening itself defining a region of sufficient weakness in said container to permit flexation of an end portion of the container about the weakened region and permit grasping of said one catheter end for removal of the catheter from the package for use; and means for releasably closing said opening to prevent contamination of the catheter.

27. A package, comprising:
an elongated catheter;
an elongated container of a flexible material resistant to the passage of bacteria, said container having a pair of end edges, a pair of side edges connecting said end edges, a pair of spaced webs, a plurality of elongated spaced ribs extending between said webs, with said webs and ribs defining a plurality of elongated contiguous cells disposed laterally across said container, with at least one generally centrally located cell being slightly larger in cross-section and longer than said catheter and containing the catheter, with the ends of said cells being closed adjacent said end edges, and with said container having a sufficient width to provide rigidity to the container and prevent excessive flexation of the container and catheter throughout a substantial longitudinal extent thereof, said container having an opening extending through the container adjacent one end of the container, with said opening being spaced from said side edges and the associated one end edge of said container, with the opening extending a sufficient distance laterally in the container to define a region of weakness in the container intermediate the opening and said side edges, and with the opening communicating between the outside of the container and a plurality of said cells at a location to expose one end of said catheter; and sheet means releasably secured to the outer surfaces of said webs around the peripheries of said opening to close said opening, said sheet being permeable to a sterilization medium and resistant to passage of bacteria, whereby said catheter may be sterilized through said sheet means and said sheet means prevents contamination of the sterile catheter prior to use, said sheet means may be removed from the outer surface of at least one of said webs to expose said one catheter end, and an end portion of the container intermediate said opening and said one end edge may be flexed about said weakness region to permit removal of the catheter from said one cell.

28. The package of claim 27 wherein each of said cells has approximately equal cross-sectional dimensions.

29. The package of claim 27 wherein a second of said cells adjacent said first cell communicates with said opening and has cross-sectional dimensions approximately equal to the dimensions of said one cell, and including a second catheter received in said second cell with one end of the second catheter exposed in said opening.

* * * * *